(12) United States Patent
Snell et al.

(10) Patent No.: US 9,415,226 B1
(45) Date of Patent: Aug. 16, 2016

(54) METHOD AND APPARATUS WITH ANODAL CAPTURE MONITORING

(75) Inventors: Jeffery D. Snell, Chatsworth, CA (US); Gene A. Bornzin, Simi Valley, CA (US); Laurence S. Sloman, West Hollywood, CA (US); Jong Gill, Valencia, CA (US)

(73) Assignee: PACESETTER, INC., Sylmar, CA (US)

( * ) Notice: Subject to any disclaimer, the term of this patent is extended or adjusted under 35 U.S.C. 154(b) by 2527 days.

(21) Appl. No.: 11/961,720

(22) Filed: Dec. 20, 2007

(51) Int. Cl.
*A61N 1/00* (2006.01)
*A61N 1/362* (2006.01)

(52) U.S. Cl.
CPC ................................. *A61N 1/3622* (2013.01)

(58) Field of Classification Search
USPC ...................... 607/28, 116, 115, 11
See application file for complete search history.

(56) References Cited

U.S. PATENT DOCUMENTS

| | | |
|---|---|---|
| 4,641,656 A | 2/1987 | Smits |
| 4,708,142 A | 11/1987 | DeCote, Jr. |
| 4,712,555 A | 12/1987 | Thornander et al. |
| 4,788,980 A | 12/1988 | Mann et al. |
| 4,809,697 A | 3/1989 | Causey, III et al. |
| 4,817,605 A | 4/1989 | Sholder |
| 4,932,407 A | 6/1990 | Williams |
| 4,940,052 A | 7/1990 | Mann et al. |
| 4,944,298 A | 7/1990 | Sholder |
| 4,944,299 A | 7/1990 | Silvian |
| 5,466,254 A | 11/1995 | Helland |
| 5,476,485 A | 12/1995 | Weinberg et al. |
| 5,522,855 A | 6/1996 | Hoegnelid |
| 5,573,550 A | 11/1996 | Zadeh et al. |
| 5,685,315 A | 11/1997 | McClure et al. |
| 5,720,768 A | 2/1998 | Verboven-Nelissen |
| 5,766,225 A | 6/1998 | Kramm |
| 5,766,229 A | 6/1998 | Bornzin |
| 5,814,079 A | 9/1998 | Kieval |
| 5,902,325 A | 5/1999 | Condie et al. |
| 6,070,100 A | 5/2000 | Bakels et al. |
| 6,122,545 A | 9/2000 | Struble et al. |
| 6,128,535 A | 10/2000 | Maarse |

(Continued)

FOREIGN PATENT DOCUMENTS

| | | |
|---|---|---|
| WO | 9929368 | 6/1999 |
| WO | 2007086782 A1 | 8/2007 |

OTHER PUBLICATIONS

Lloyd, Michael S. MD et al., "Reverse Polarity Pacing: The Hemodynamic Benefit of Anodal Currents at Lead Tips for Cardiac Resynchronization Therapy," J Cardiovasc Electrophysiol. Nov. 2007;18:1167-1171.

(Continued)

*Primary Examiner* — Nicole F Lavert

(57) ABSTRACT

During cross-chamber pacing, where anodal capture may not be desirable, pulses are applied between a cathode electrode in a first chamber and an anode electrode in a second chamber. A capture detector detects for capture of the second chamber by the pacing pulses. If capture of the second chamber persists, another electrode is selected as the anodal electrode. During single-chamber pacing, where anodal capture may be desirable, pulses are applied between a cathode electrode and an anode electrode associated with the same chamber. A capture detector detects for capture at both electrodes. If anodal capture is not detected, the energy of the pacing pulse is increased, until anodal capture is detected.

18 Claims, 4 Drawing Sheets

(56) References Cited

U.S. PATENT DOCUMENTS

| | | | |
|---|---|---|---|
| 6,169,921 | B1 | 1/2001 | KenKnight et al. |
| 6,181,968 | B1 | 1/2001 | Limousin |
| 6,208,895 | B1 | 3/2001 | Sullivan et al. |
| 6,278,894 | B1 | 8/2001 | Salo et al. |
| 6,295,470 | B1 | 9/2001 | Mower |
| 6,456,878 | B1 | 9/2002 | Yerich et al. |
| 6,473,645 | B1 | 10/2002 | Levine |
| 6,611,712 | B2 | 8/2003 | Spinelli et al. |
| 6,687,545 | B1 | 2/2004 | Lu |
| 7,110,815 | B2 | 9/2006 | Heil, Jr. et al. |
| 7,191,003 | B2 | 3/2007 | Greenhut et al. |
| 2002/0078968 | A1 | 6/2002 | Spinelli et al. |
| 2004/0030359 | A1* | 2/2004 | Spinelli et al. .................. 607/27 |
| 2005/0277993 | A1 | 12/2005 | Mower |
| 2006/0287685 | A1* | 12/2006 | Meyer et al. .................... 607/28 |
| 2006/0293717 | A1* | 12/2006 | Sathaye et al. .................. 607/28 |
| 2007/0239215 | A1 | 10/2007 | Bhunia et al. |

OTHER PUBLICATIONS

Thakral, Anshul et al., "Effects of anodal vs. cathodal pacing on the mechanical performance of the isolated rabbit heart," J Appl Physiol. 2000;89:1159-1164.

Thakor, Nitish PhD et al., "Effect of Varying Pacing Waveform Shapes on Propagation and Hemodynamics in the Rabbit Heart," Am J Cardiol 1997;79(6A):36-43.

* cited by examiner

METHOD AND APPARATUS WITH ANODAL CAPTURE MONITORING

FIELD OF THE INVENTION

This invention relates generally to cardiac stimulation devices and associated methods involving monitoring capture following delivery of a pacing pulse. More specifically the present invention relates to stimulation devices that provide one or more of cross-chamber stimulation and single chamber stimulation, with anodal capture detection.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices may incorporate both a pacemaker and a defibrillator.

In general, the pacing function of implantable cardiac devices is provided by two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing and/or sensing electrode configurations. In the unipolar configuration, the pacing stimulation pulses are applied, or intrinsic responses are sensed, between a single electrode carried by the lead, in electrical contact with the desired heart chamber, and the pulse generator case. The electrode serves as the cathode (negative pole) and the case serves as the anode (positive pole). In the bipolar configuration, the pacing stimulation pulses are applied, or intrinsic responses are sensed, between a pair of closely spaced electrodes carried by the lead, in electrical contact with the desired heart chamber, with the most proximal electrode serving as the anode and the most distal electrode serving as the cathode.

Implantable cardiac devices deliver pacing pulses to the heart to induce a depolarization and a mechanical contraction of that chamber when the patient's own intrinsic rhythm fails. To this end, these devices include sensing circuits that sense cardiac activity for the detection of intrinsic cardiac events such as intrinsic atrial events (P waves) and intrinsic ventricular events (R waves). By monitoring P waves and/or R waves, the cardiac device circuits are able to determine the intrinsic rhythm of the heart and provide stimulation pacing pulses that force atrial and/or ventricular depolarizations at appropriate times in the cardiac cycle when required, to help stabilize the electrical rhythm of the heart.

Pacing systems may function as single-chamber, dual-chamber, or biventricular systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Biventricular systems stimulate in corresponding chambers of the heart as, for example, the right ventricle (RV) and left ventricle (LV).

Biventricular pacing has been shown to coordinate contractions of the left and right ventricles, reduce the amount of blood flow that leaks through the mitral valve, and decreases the motion of the septal wall that separates the chambers of the heart. Such motion can affect the quantity of blood that the ventricle can pump out in a single beat.

Biventricular pacing has been found to be particularly advantageous in patient's suffering from congestive heart disease because of the improved ability of the left ventricle to fully pump blood from the heart. As a result, patients are able to tolerate greater exertion, have a longer life span, and experience a higher quality of life.

Biatrial pacing has also been suggested to also lend in coordinating contractions of the right and left atria. As used herein, the term corresponding chambers is meant to refer to either the right and left atria or the right and left ventricle.

With the ability to pace either or both sets of corresponding heart chambers, it is believed that a wide variety of irregular heart conditions may be most efficiently addressed. For example, in a patient suffering from dilated cardiomyopathy, typically the left ventricle is predominately affected in the earlier stages of the disease. The dilated left ventricle has diminished contractility causing its contraction to be slower and weaker than the still healthy right ventricle. Thus, by selecting the stimulation pathway direction from the left ventricle to the right ventricle, the slower left ventricle contraction is initiated prior to the faster right ventricle contraction, yielding superior synchronization of right ventricle and left ventricle contractions.

Traditional unipolar pacing of the left ventricle entails applying a pacing pulse between a left ventricle tip electrode carried on a lead implanted in the coronary sinus of the heart and serving as the cathode and the conductive enclosure of the implantable cardiac stimulation device serving as the anode. The distance between these electrodes can require substantial energy to achieve reliable capture of the left ventricle. These energies could cause contraction of chest muscle resulting in discomfort to a patient.

To avoid such high pacing energies, cross chamber pacing has been performed. Here, to pace the left ventricle, for example, instead of using the device enclosure as the anodal pacing electrode, an electrode carried on a separate lead and implanted in the right ventricle, such as the right ventricular ring electrode, is enlisted as the left ventricular anodal pacing electrode. This has been found to lower pacing energy requirements for left ventricular pacing. However, it has also been found that anodal capture may occur at the right ventricular electrode thereby resulting in simultaneous pacing of the right ventricle with the left ventricle. If permitted, this would subvert the desire to pace the ventricles separately and, more particularly, the left ventricle before the right ventricle.

While anodal capture may be undesirable in the case of cross-chamber stimulation, it may prove beneficial in single chamber stimulation. For example, in the case of left ventricular pacing, simultaneous, multisite stimulation, i.e., both anodal capture and cathode capture, of the left ventricle may provide improved left ventricular contraction.

Accordingly, there is a need for cardiac stimulation devices and related methods that provide for anodal capture detection. In the case of cross-chamber stimulation, there is a further need for devices and methods that operate to prevent anodal capture. In the case of single chamber stimulation, there is a further need for devices and methods that operate to provide anodal capture. Various aspects of the present invention fulfill each of these needs.

SUMMARY OF THE INVENTION

One aspect of the invention relates to implantable cardiac stimulation devices and associated methods that operate to prevent anodal capture during cross-chamber pacing. One such device includes a first chamber lead including a first electrode that electrically couples to a first chamber of a heart, and a second chamber lead including a second electrode that electrically couples to a second chamber of the heart. The device further includes a pulse generator that provides for the delivery of pacing pulses between the first and second electrodes with the second electrode being an anodal electrode, and a capture detector that detects for capture of the second chamber by the pacing pulses.

An associated method of pacing a heart to avoid anodal capture during cross-chamber pacing includes applying pacing pulses between a first chamber and a second chamber of a heart with a first-chamber first electrode and a second-chamber second electrode, the second electrode being an anode. The method further includes detecting capture of the second chamber by the pacing pulses.

Another aspect of the invention relates to implantable cardiac stimulation devices and associated methods that operate to provide anodal and cathodal capture during single chamber pacing. One such device includes an anode electrode and a cathode electrode that electrically couple to a same chamber of a heart and a pulse generator that provides pacing pulses between the anode electrode and the cathode electrode. The device further includes a capture detector that detects for capture at both the anode electrode and the cathode electrode by the pacing pulses.

An associated method includes applying a first pacing pulse of a first energy level between an anode electrode and a cathode electrode, each electrode electrically coupled to a same heart chamber. The method further includes detecting for capture at both the anode electrode and the cathode electrode by the first pacing pulse; and if capture is not detected at one or both of the anode electrode and the cathode electrode, applying a second pacing pulse between the anode electrode and the cathode electrode, the second pacing pulse having a second energy level greater than the first energy level.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
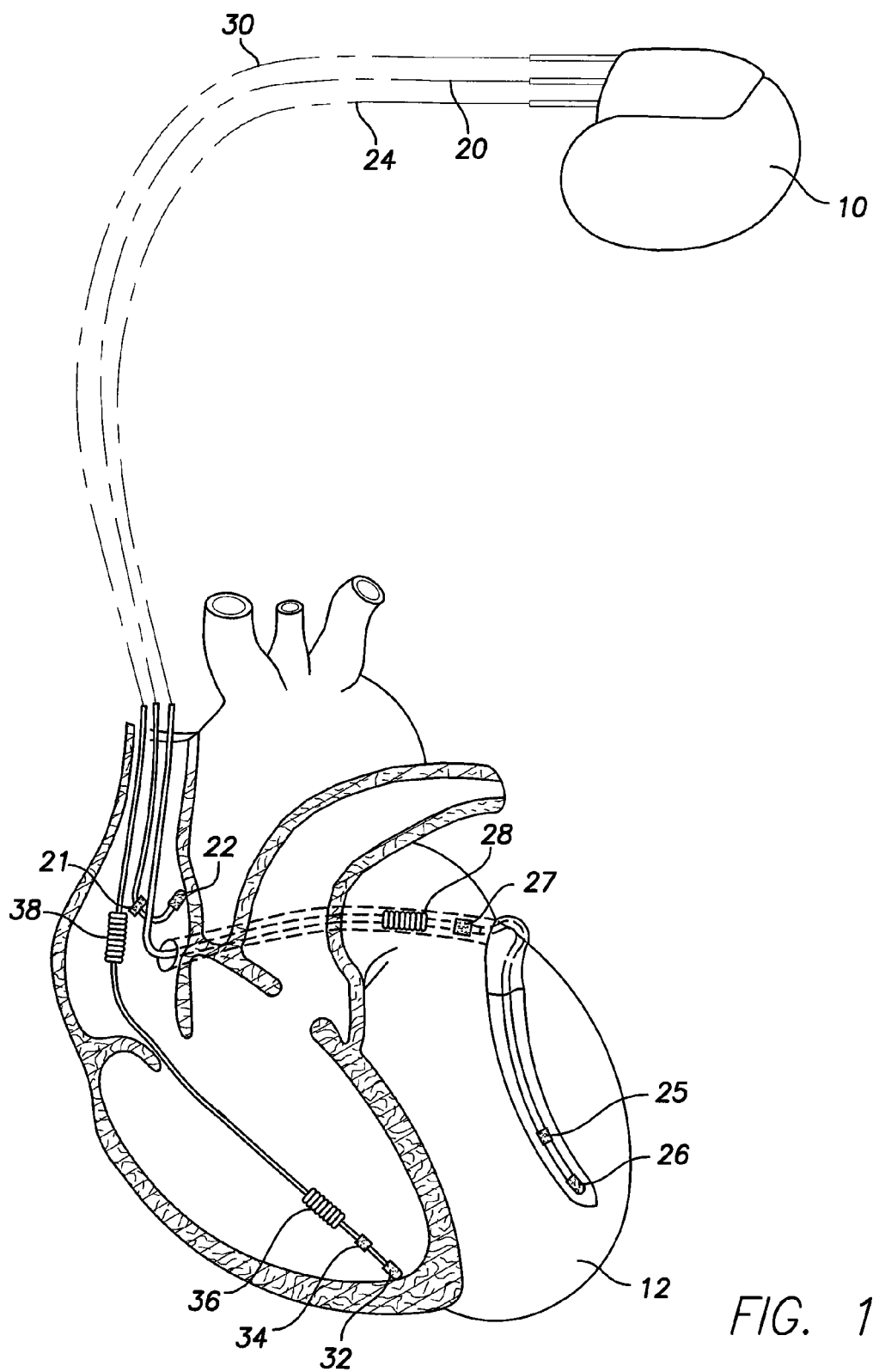
FIG. 1 is a simplified diagram illustrating an implantable stimulation device according to an embodiment of the invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, for unipolar sensing and pacing and which typically is implanted in the patient's right atrial appendage. The lead 20 may further include an atrial ring electrode 21 to enable bipolar sensing and pacing in the right atrium.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which is hereby incorporated by reference. The lead 24 may further include a left ventricular ring electrode 25. The electrode 25 may be employed to provide bipolar sensing and pacing with electrode 26 or cross-chamber pacing during biventricular pacing.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC/right atrial coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
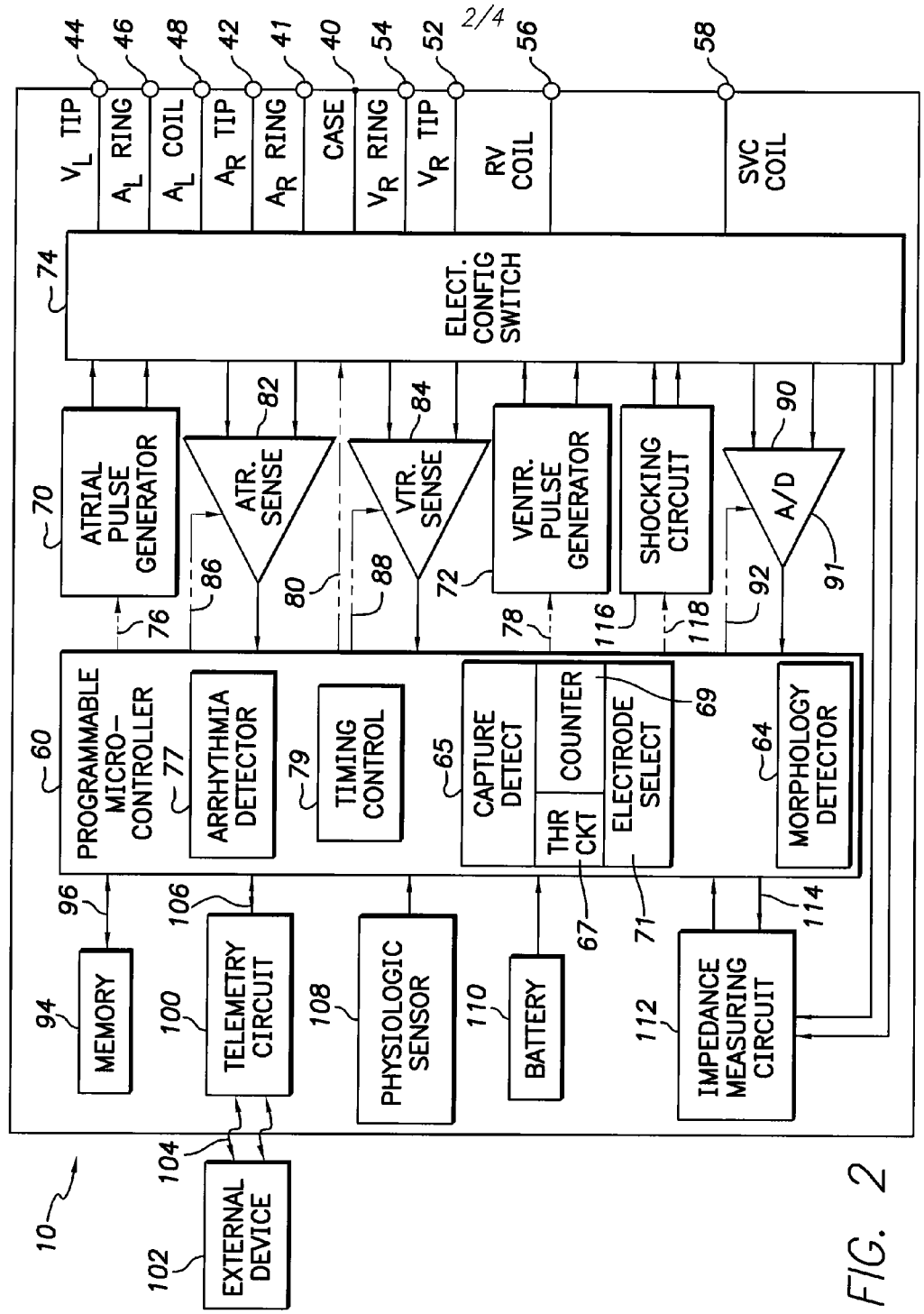
FIG. 2 is a functional block diagram of the multi-chamber implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 41, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring terminal 41 adapted for connection to the atrial ring electrode 21.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. The connector may further include a terminal (not shown) for connection to electrode 25.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits 82, 86, as is known in the art.

For arrhythmia detection, the device 10 includes an arrhythmia detector 77 that utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of a data acquisition system 90. The data acquisition system 90 includes an analog-to-digital (A/D) and sense circuit 91 that is configured to acquire intracardiac electrogram (IEGM) signals, convert the raw analog data into a digital signal, and store the digital signals for later processing such as, for example, in capture detection, and/or telemetric transmission to an external device 102. The data acquisition system sense circuit 91 is coupled to the right atrial lead 20, the coronary sinus lead 24, and the right ventricular lead 30 through the switch 74 to sample cardiac signals across any pair of desired electrodes.

In accordance with the present invention, the data acquisition system 90 may be employed to record an IEGM signal during a window following delivery of a pacing pulse to enable a capture detector 65 to detect capture of a desired chamber of the heart in response to the applied pacing stimulus. Capture occurs when an electrical stimulus applied to the heart is of sufficient energy to depolarize the cardiac tissue, thereby causing the heart muscle to contract. The microcontroller 60 enables capture detection when a pulse generator generates a stimulation pulse. During the stimulation pulse, the inputs to the sense circuit 91 are shorted (blanking period). After the stimulation pulse, the microcontroller 60 starts a detection window of, for example, 64 mS, using the timing control circuitry 79 within the microcontroller 60. During this window, the data acquisition system 90 via control signal 92 samples the IEGM signal that falls in the capture detection window and stores the IEGM in memory 94. Thereafter, the microcontroller 60 processes the IEGM to obtain a measurement related to capture. For example, microcontroller 60 may integrate the stored IEGM with respect to a baseline established during the blanking period. If the resulting integral is greater than a threshold determined by a threshold circuit 67, capture is deemed to have occurred. The threshold may be set manually through programming or automatically by the threshold circuit 67 to eliminate false positives. Capture detection in accordance with this embodiment may occur on a beat-by-beat basis or on a sampled basis, as for example, every Nth beat.

Capture detection may be employed in conducting capture threshold searches. Preferably, a capture threshold search is performed once a day during at least the acute phase (e.g., the first 30 days) and less frequently thereafter. A capture threshold search would begin at a desired energy level starting point (either a high energy level or the level at which capture is currently occurring) and decrease until capture is lost. The value at which capture is lost is known as the capture threshold. Thereafter, a safety margin is added to the capture threshold.

The microcontroller 60 is further coupled to the memory 94 by a suitable data/address bus 96, wherein the programmable operating parameters used by the microcontroller 60, including a manually selected capture detection threshold, are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 may also be used for detecting capture in an alternative embodiment of the present invention.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

It will also be noted in FIG. 2 that the device 10 further includes a counter 69 and an electrode selector 71. The counter 69 may be used to count recorded captures of a given chamber following the application of a pacing pulse. The electrode selector 71, in response to the counter achieving a given count, may then select another or alternative electrode for future pacing.

In order to avoid applying pacing pulses between electrode 26 (FIG. 1) and the case electrode 40 (FIG. 2) to pace the left ventricle, the right ventricular ring electrode 34 may be used instead of the case electrode to serve as the anodal electrode with electrode 26 as the cathodal electrode. This would help reduce the energy required for capture of the left ventricle and also avoid contraction of chest muscle and the perceived discomfort which may result therefrom. However, if pacing with electrode 34 as the anode causes capture of the anodal chamber, here the right ventricle, the object of pacing the left ventricle before pacing the right ventricle in biventricular pacing is subverted.

Accordingly, in accordance with an aspect of the present invention, anodal capture detection is carried out during cross-chamber stimulation to prevent capture of the anodal chamber, i.e., the chamber with which the anodal electrode is associated. For example, anodal capture detection may be carried out to determine if the right ventricle is being captured when the left ventricle is paced with pacing pulses applied cross-chamber, between tip electrode 26 and ring electrode 34. For such capture detection, which may be carried out as previously described, the sense circuit 91 may be connected by switch 74 to electrode 34 and the case electrode 40. Alternatively, the sense circuit 91 may be connected to electrodes 32 and 34 for the capture detection.

Upon each detection of capture of the right ventricle, the capture may be recorded and counted by counter 69. When the counter reaches a given number, the electrode selector 71 may then select another electrode to serve as an anodal electrode with cathodal electrode 26. For example, the another anodal electrode may be the case electrode 40, the atrial ring electrode 21, or the coil electrode 38.

It is to be understood that the present invention is not limited to detection of capture of the right ventricle only upon left ventricular, cross-chamber pacing. Those skilled in the art will appreciate that the present invention may be applied to other dispersed non-traditional unipolar configurations as well, such as, for example, in pacing the right ventricle with a cathodal right ventricular tip electrode, such as electrode 32, and an anodal left ventricular ring, such as electrode 25, during biventricular pacing. Capture detection here would be of the left ventricle and be done by sensing between the left ventricular ring electrode 25 and the case electrode 40, for example. Another example would be in pacing the right atrium with a cathodal right atrial tip electrode, such as electrode 22, and an anodal right ventricular ring electrode, such as electrode 34. Here, capture of the right ventricle would be of concern and such capture detection may be carried out by sensing between the right ventricular ring electrode 34 and the tip electrode 32 or case electrode 40.

Figure 3:
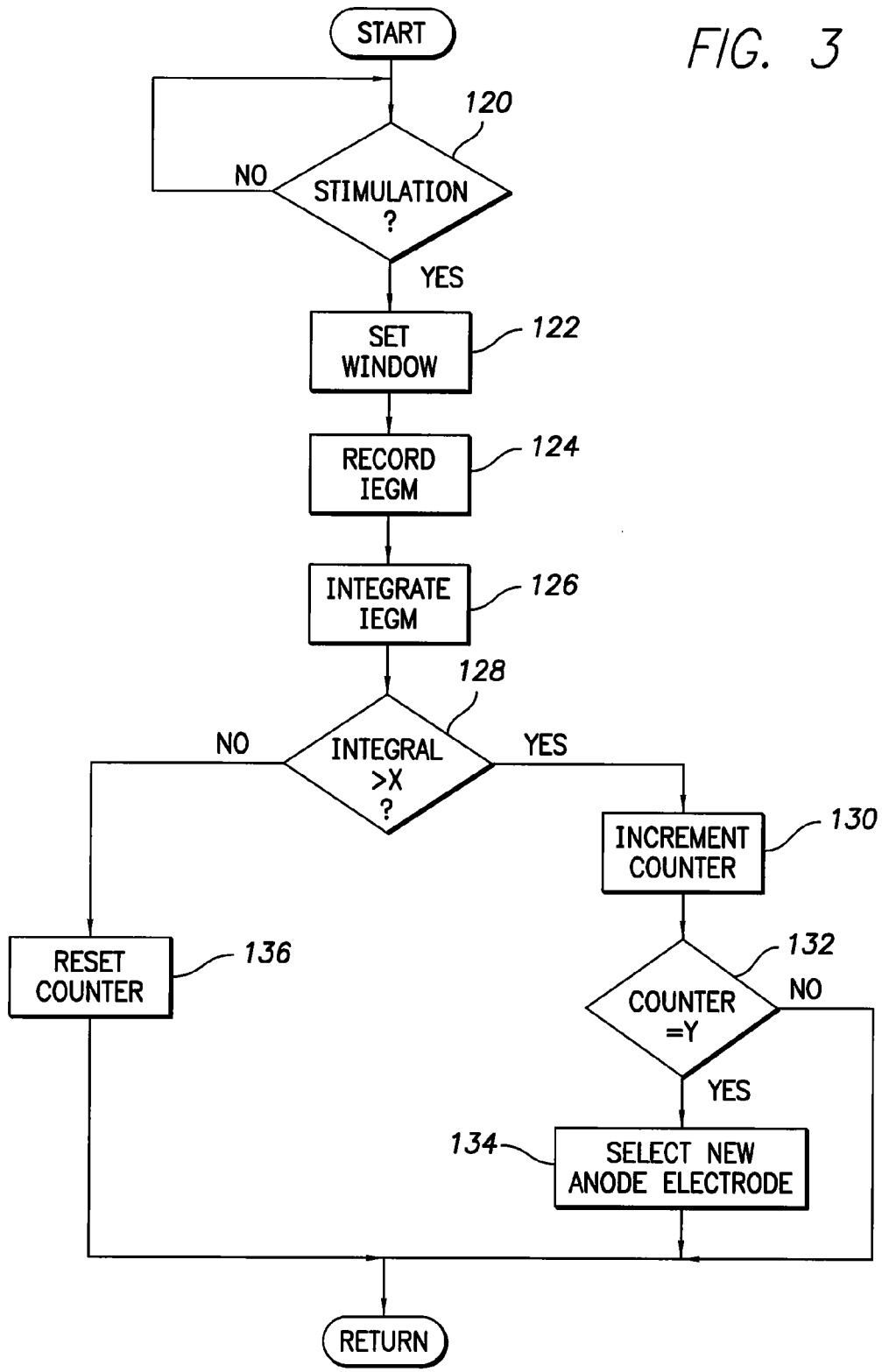
FIG. 3 is a flow chart describing an overview of device operation related to preventing anodal capture during cross-chamber stimulation.

Referring now to FIG. 3, a flow chart describing an overview of the operation and novel features implemented in one embodiment of the invention by device 10 is shown. In this flow chart, the various algorithmic steps are summarized in individual "blocks". Such blocks describe specific actions or decisions that must be made or carried out as the algorithm proceeds. Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates with decision block 120. Here, the capture detector 65 determines if a stimulation pulse is to be applied to the left ventricle with electrode 26 being a cathode and electrode 34 being an anode. When the decision is affirmative, the process advances to activity block 122 where the capture detector 65 sets the sensing window of, for example, 64 mS. The process then advances to activity block 124 where the capture detector 65 causes the sense circuit 91 to sense cardiac activity of the right ventricle. To record the resulting IEGM, the sense circuit 91 of the acquisition system 90 is preferably connected to electrode 34 and the case electrode 40.

After the IEGM is recorded, the process advances to activity block 126 wherein the stored IEGM is integrated. Once the integration is completed, the process advances to decision block 128 where it is determined if the resulting integral is greater than the manually or automatically set threshold (X). If it is, capture of the right ventricle as a result of the left ventricular cross-chamber pacing pulse is deemed to have occurred. Accordingly, in activity block 130 the counter 69 is incremented.

Next, in decision block 132, it is determined by the electrode selector 71 if the count in counter 69 is now equal to a given number (Y). If the count is not equal to the number (Y), the process returns. If it is, the electrode selector 71 then proceeds in block 134 to select another electrode to serve as the anodal electrode in place of electrode 34. The process then returns. Upon returning, the process reinitiates as programmed. This may be on a beat-by-beat basis or less often Hence, in this embodiment, a given number of consecutive right ventricle captures are required before another electrode is selected as the anodal electrode. However, of course, this may be varied as desired. The given number (Y) may be varied as well as the level of consistent captures before a new electrode is selected as the anode.

Returning to decision block 128, if it is determined that the integral of the stored IEGM is less than the set threshold (X), the process advances to activity block 136 to reset the counter before returning.

In accordance with another aspect of the invention, capture detection is carried out to determine if a single chamber is captured at both an anode electrode and a cathode electrode when the chamber is paced with a pacing pulse applied between the electrodes, each of which are in contact with cardiac tissue. For example, with respect to a coronary sinus lead placed with respect to the left ventricle, a pacing pulse may be applied between a cathodal tip electrode 26 and an anodal ring electrode 25, each of which are in contact with left-ventricular tissue, either directly or through vascular tissue.

Subsequent to the application of the pacing pulse, capture is detected for, at the cathode electrode 26 without using the anode electrode 25. In a preferred embodiment, capture is detected at each electrode independently, using separate sense circuitry. For example, with reference to FIG. 2, a first sense circuit 91 may be connected by switch 74 to cathode electrode 26 and the case electrode 40 or any other electrode other than the anode electrode 25 to detect for capture at the cathode electrode. Likewise, capture is detected for, at the anode electrode 25 without using the cathode electrode 26. For such anode capture detection, a second sense circuit (not shown) may be connected by switch 74 to anode electrode 25 and the case electrode 40 or any other electrode other than the cathode electrode 26.

It is to be understood that this aspect of the invention is not limited to detection of anode and cathode capture of the left ventricle when bipolar pacing the left ventricle. Those skilled in the art will appreciate that the present invention may be applied to other dispersed bipolar configurations—provided the anode electrode and cathode electrode are positioned in contact with, or substantially adjacent to, cardiac tissue—as opposed to being suspended in a blood pool—so as to provide the proper medium for capture detection. For example, anode and cathode detection may be used when pacing the right ventricle with a cathodal right ventricular tip electrode, such as electrode 32, and an anodal right ventricular ring, such as electrode 34—provided the ring electrode 34 is in contact with cardiac tissue. Another example would be in pacing the right atrium with a cathodal right atrial tip electrode, such as electrode 22, and an anodal right atrial ring electrode, such as electrode 24—provided the ring electrode 34 is in contact with cardiac tissue.

Figure 4:
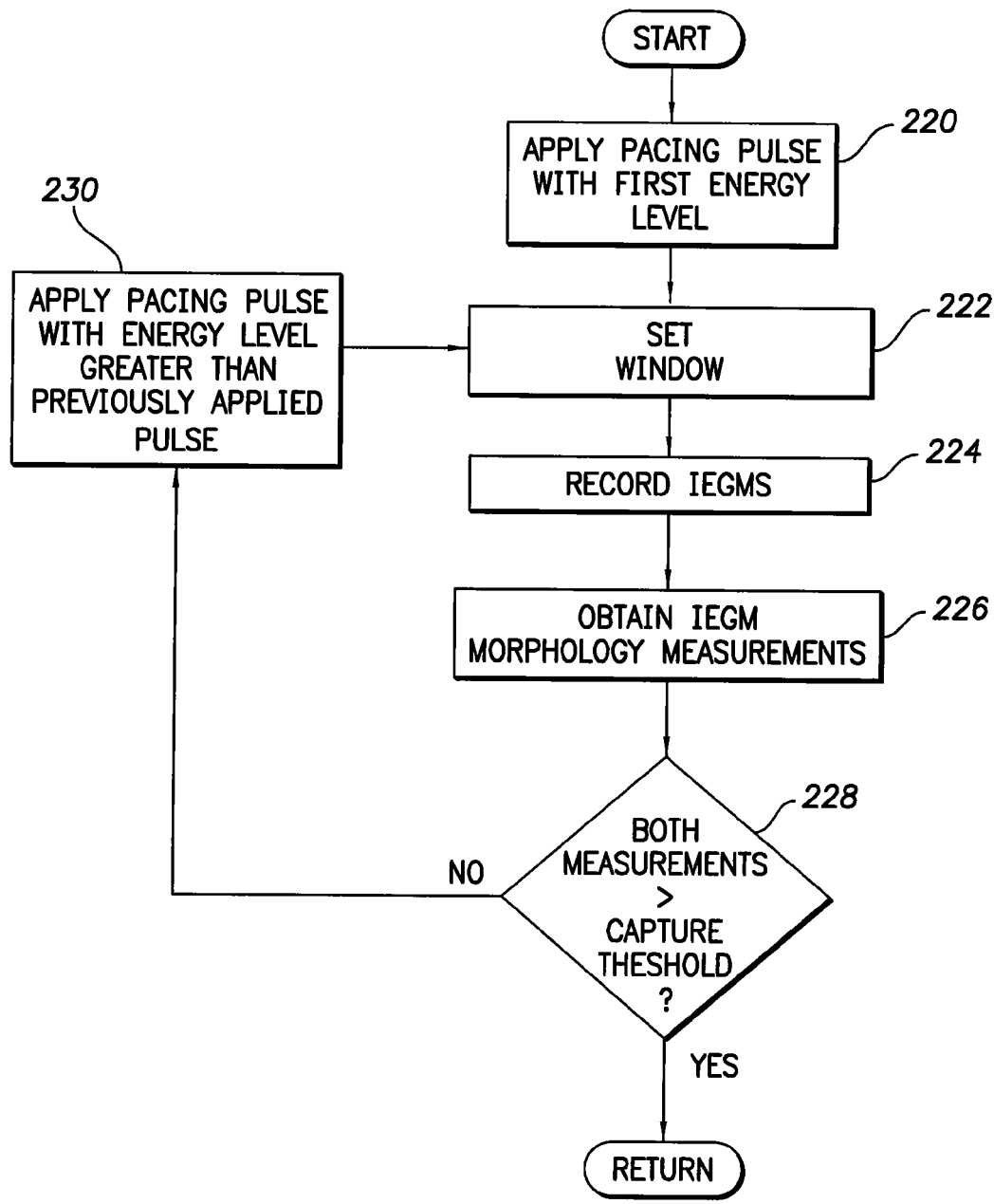
FIG. 4 is a flow chart describing an overview of device operation related to providing anodal capture and cathodal capture detection during single chamber stimulation.

Referring now to FIG. 4, a flow chart describing an overview of the operation and features implemented in one embodiment of the invention by device 10 is shown. In this flow chart, the various algorithmic steps are summarized in individual "blocks". Such blocks describe specific actions or decisions that must be made or carried out as the algorithm proceeds. Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow charts and other descriptions presented herein.

With reference to FIG. 4, at block 220 a stimulation pulse having a first energy level is applied to the left ventricle with electrode 26 being a cathode and electrode 25 being an anode. At block 222, the capture detector 65 sets a sensing window of length sufficient to sense capture at both the anode electrode and the cathode electrode. At block 224, IEGMs are recorded for each of the anode electrode and the cathode electrode, preferable using separate sense circuits, each connected between one of the electrodes and the case electrode 40.

At block 226, the anode IEGM and the cathode IEGM are individually processed to obtain morphology measurements related to capture detection. For example, the IEGMs may be integrated. Alternatively, a peak voltage may be determined. At decision block 228, each of the resulting IEGM measurements is compared to a threshold indicative of capture. In the case of voltage measurement, the peak voltage of the cathodal IEGM is compared to a cathodal threshold, which is typically 0.7 to 1.5 volts. The peak voltage of the anodal IEGM is compared to an anodal threshold, which is typically 1.2 to 2.2 volts. If each measurement satisfies its respective threshold, capture at both the anodal electrode and the cathodal electrode, i.e., multisite capture, is deemed to have occurred. Accordingly, the process returns. Upon returning, the process reinitiates as programmed. This process of multisite capture verification may occur on a beat-by-beat basis or periodically, such as every Nth beat or every Nth pacing-pulse delivery.

If one or both of the IEGM measurements do not satisfy their respective threshold, multisite capture is deemed not to have occurred. In this case, at block 230, a pacing pulse of a second energy level greater than the first energy level is applied between the anodal electrode 25 and the cathodal electrode 26. The process then returns to block 222 where the capture detection process is repeated. The overall process repeats with successive, incremental increases in pacing pulse energy until multisite capture is detected.

In the case where multisite capture is detected initially, it may be desirable to reduce the energy of the pacing pulse to a level just sufficient to provide multisite capture in order to conserve energy. Accordingly, an alternative process may involve—upon multisite capture detection—reducing the pacing-pulse energy and repeating the capture detection process until multisite capture is lost. Once multisite capture is lost, the pacing pulse energy may then be incrementally increased to a level sufficient to obtain multisite capture again.

In an alternate configuration, capture at the anode electrode and the cathode electrode may be detected for, using the same sensing circuitry electrically couple between the electrodes. In this case, the morphology of the sensed IEGM is compared to a different template morphologies corresponding to no capture, cathodal capture only and both cathodal and anodal capture.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   a first chamber lead including a first electrode that electrically couples to a first chamber of a heart;
   a second chamber lead including a second electrode that electrically couples to a second chamber of the heart;
   a pulse generator that provides pacing pulses between the first and second electrodes with the second electrode being an anodal electrode, wherein the pacing pulses are adapted to induce a depolarization and a mechanical contraction of the first chamber of the heart; and
   a capture detector adapted to detect capture of the second chamber by the pacing pulses.

2. The device of claim 1 wherein the first electrode is a tip electrode and the second electrode is a ring electrode.

3. The device of claim 1 wherein the capture detector includes a sense circuit coupled to the second electrode.

4. The device of claim 1 wherein the capture detector includes a sense circuit, the second electrode is a ring electrode, the second-chamber lead further includes a tip electrode, and the sense circuit is coupled to the tip electrode and the ring electrode.

5. The device of claim 1 further comprising a case electrode, wherein the capture detector includes a sense circuit that is coupled to the case electrode and the second electrode.

6. The device of claim 1 wherein the first-chamber lead is a left ventricular lead and the second-chamber lead is a right ventricular lead.

7. The device of claim 1 further comprising a memory that stores a record of detected second chamber captures by the pacing pulses.

8. The device of claim 1 further comprising an electrode selector that selects another anode electrode responsive to a given number of second-chamber captures by the pacing pulses.

9. The device of claim 1 wherein the capture detector detects for capture of the second chamber on a beat-by-beat basis.

10. The device of claim 1 wherein the capture detector detects for capture of the second chamber on every Nth heartbeat.

11. The device of claim 1 wherein the capture detector includes a threshold circuit having a manually settable threshold.

12. The device of claim 1 wherein the capture detector includes a threshold circuit having an automatically settable threshold.

13. An implantable cardiac stimulation device comprising:
 a first electrode that electrically couples to a first chamber of a heart;
 a second electrode that electrically couples to a second chamber of the heart;
 a pulse generator that provides pacing pulses between the first and second electrodes with the second electrode being an anodal electrode, wherein the pacing pulses are adapted to induce a depolarization and a mechanical contraction of the first chamber of the heart; and
 a capture detector adapted to detect capture of the second chamber by the pacing pulses using at least one second-chamber electrode.

14. The device of claim 13 wherein the at least one second-chamber electrode comprises the second electrode.

15. The device of claim 13 wherein the at least one second-chamber electrode comprises any electrode that electrically couples to the second chamber, other then the second electrode.

16. The device of claim 13 further comprising a case electrode and wherein the capture detector detects for capture of the second chamber by the pacing pulses using one second-chamber electrode and the case.

17. The device of claim 16 wherein the second-chamber electrode comprises the second electrode.

18. The device of claim 16 wherein the second-chamber electrode comprises any electrode that electrically couples to the second chamber, other then the second electrode.

* * * * *